US006608058B2

(12) United States Patent
Yoon et al.

(10) Patent No.: US 6,608,058 B2
(45) Date of Patent: Aug. 19, 2003

(54) 6-METHYLNICOTINAMIDE DERIVATIVES AS ANTIVIRAL AGENTS

(75) Inventors: Sung-June Yoon, Seoul (KR); Sang-Wook Lee, Anyang-si (KR); Jin-Soo Lee, Anyang-si (KR); Nam-Doo Kim, Inchon-si (KR); Geun-Hyung Lee, Anyang-si (KR); Hak-Dong Lee, Anyang-si (KR); Jong-Woo Kim, Anyang-si (KR); Sang-Jin Park, Seoul (KR); Hee-Jeong Park, Anyang-si (KR)

(73) Assignee: Dong Wha Pharm. Ind. Co., Ltd., Seoul (KR)

( * ) Notice: Subject to any disclaimer, the term of this patent is extended or adjusted under 35 U.S.C. 154(b) by 31 days.

(21) Appl. No.: 10/257,216
(22) PCT Filed: Apr. 13, 2001
(86) PCT No.: PCT/KR01/00613
§ 371 (c)(1),
(2), (4) Date: Oct. 10, 2002
(87) PCT Pub. No.: WO01/78648
PCT Pub. Date: Oct. 25, 2001

(65) Prior Publication Data

US 2003/0092709 A1 May 15, 2003

(30) Foreign Application Priority Data

Apr. 17, 2000 (KR) .......................................... 2000/20137
Jun. 10, 2000 (KR) ........................................ 2000/31926

(51) Int. Cl.$^7$ .................. A61K 31/5377; A61K 31/455; C07D 401/12; C07D 413/14
(52) U.S. Cl. .................... 514/234.5; 544/131; 544/365; 546/193; 546/256; 546/275.7
(58) Field of Search .......................... 544/131; 546/256, 546/275.7; 514/234.5

(56) References Cited

U.S. PATENT DOCUMENTS 5,424,432 A    6/1995    Fredenburgh et al.

FOREIGN PATENT DOCUMENTS

| EP | 0 563 732 A1 | 3/1993 |
| EP | 0 563 734 A1 | 3/1993 |
| WO | WO 97/03071 | 7/1996 |

*Primary Examiner*—Robert W. Ramsuer
(74) *Attorney, Agent, or Firm*—Muserlian, Lucas and Mercanti, LLP

(57) ABSTRACT

The present invention relates to novel 6-methylnicotinamide derivatives and their pharmaceutically acceptable salts, the process for preparing them, and the pharmaceutical compositions containing said compounds as active ingredients. The 6-methylnicotinamide derivatives of the present invention exhibit their inhibitory activity against the proliferation of human immunodeficiency virus (HIV) as well as hepatitis B virus (HBV) and hepatitis C virus (HCV), such that they can be used for hepatitis B, hepatitis C and acquired immune deficiency syndrome (AIDS).

8 Claims, No Drawings

6-METHYLNICOTINAMIDE DERIVATIVES AS ANTIVIRAL AGENTS

This patent application claims a benefit of priority from Korean Patent Application No. 2000/20137 filed Apr. 17, 2000 and Korean Patent Application No. 2000/31926 filed Jun. 10, 2000 through PCT Application Serial No. PCT/KR01/00613 filed Apr. 13, 2001, the contents of each of which are incorporated herein by reference.

TECHNICAL FIELD

The present invention relates to novel 6-methylnicotinamide derivatives and pharmaceutical compositions containing said derivatives. More specifically, the present invention relates to novel 6-methylnicotinamide derivatives and their pharmaceutically acceptable salts represented below in formula 1, which have an excellent inhibitory effect on proliferation of hepatitis B virus(HBV), hepatitis C virus(HCV) and human immunodeficiency virus (HIV). The present invention also relates to the process for preparing compounds of formula 1 and the pharmaceutical compositions containing said derivatives as effective ingredients against viruses.

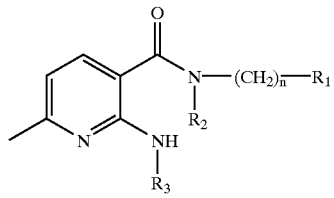

Formula 1 wherein, $R_1$ is hydroxy group; straight or branched $C_1$~$C_5$ alkyl group; $C_3$~$C_6$ cycloalkyl group which is unsubstituted or substituted with hydroxy group, $C_2$~$C_6$ dialkylamino group; saturated or unsaturated 5 or 6 membered heterocyclic compounds containing 1 to 2 heteroatoms selected from N, O and S which may be unsubstituted or substituted with $C_1$~$C_3$ alkyl group; or

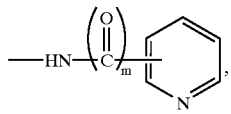

m is an integer of 0 or 1, $R_2$ is H or $C_1$~$C_4$ alkyl group;

or $R_1$ and $R_2$ are joined to form a 5- or 6-membered heterocyclic ring containing 1 to 2 heteroatoms selected from N, O and S, n is an integer from 0 to 4, $R_3$ is 5-indazole or 6-indazole

BACKGROUND OF THE INVENTION

Hepatitis B virus (HBV; referred as "HBV" hereinafter) causes acute or chronic hepatitis, which may progress to liver cirrhosis and liver cancer. It is estimated that three hundred million people are infected with HBV in the world (Tiollais & Buendia, Sci. Am., 264, 48, 1991). There has been much research about the molecular biological characteristics of HBV and their relationship to liver diseases in order to find ways to prevent and treat hepatitis B. Various vaccines and diagnostic drugs have been developed and much effort is being channeled into research to find treatment for hepatitis B.

HBV genome consists of genes for polymerase (P), surface protein (pre-S1, pre-S2 and S), core protein (pre-C and C), and X protein. Of these proteins expressed from HBV genes, polymerase, surface protein, and core protein are structural proteins and X protein has a regulatory function.

The gene for HBV polymerase comprises 80% of the whole virus genome and produces a protein of 94 kD size with 845 amino acids, which has several functions in the replication of virus genome. This polypeptide includes sequences responsible for activities of protein primer, RNA dependent DNA polymerase, DNA dependent DNA polymerase, and RNase H. Kaplan and his coworkers first discovered reverse transcriptase activities of polymerase, which led to much research in replicating mechanism of HBV.

HBV enters liver when antigenic protein on virion surface is recognized by hepatic cell-specific receptor. Inside the liver cell, DNAs are synthesized by HBV polymerase action, attached to short chain to form complete double helix for HBV genome. Completed double helical DNA genome of HBV produces pre-genomic mRNA and mRNAs of core protein, surface protein, and regulatory protein by the action of RNA polymerase. Using these mRNAs, virus proteins are synthesized. Polymerase has an important function in the production of virus genome, forming a structure called replicasome with core protein and pre-genomic mRNA. This process is called encapsidation. Polymerase has repeated units of glutamic acid at the 3'-end with high affinity for nucleic acids, which is responsible for facile encapsidation. When replicasome is formed, (–) DNA strand is synthesized by reverse transcribing action of HBV polymerase and (+) DNA strand is made through the action of DNA dependent DNA polymerase, which in turn produces pre-genomic mRNAs. The whole process is repeated until the pool of more than 200 to 300 genomes is maintained (Tiollais and Buendia, Scientific American, 264: 48–54, 1991).

Although HBV and HIV are different viruses, the replication mechanisms during their proliferation have some common steps, namely, the reverse transcription of virus RNA to form DNA and the removal of RNA strand from subsequently formed RNA-DNA hybrid.

Recently, nucleoside compounds such as lamivudine and famvir have been reported to be useful inhibitors of HBV proliferation, although they have been originally developed as therapeutics for the treatment of acquired immune deficiency syndrome (AIDS; referred as "AIDS" hereinafter) and herpes zoster infection (Gerin, J. L, Hepatology, 14: 198–199, 1991; Lok, A. S. P., J. Viral Hepatitis, 1: 105–124, 1994; Dienstag, J. L. et al., New England Journal of Medicine, 333: 1657–1661, 1995). However, these nucleoside compounds are considered a poor choice for treatment of hepatitis B because of their high cost and side effects such as toxicity, development of resistant virus and recurrence of the disease after stopping treatment. Effort to find therapeutics for hepatitis B among non-nucleoside compounds has been continued and antiviral effects against HBV have been reported for quinolone compounds (EPO 563732, EPO 563734), iridos compounds (KR 94-1886), and terephthalic amide derivatives (KR 96-72384, KR 97-36589, KR 99-5100). In spite of much effort, however, effective drugs for treating hepatitis B have not been developed yet and therapeutic method mainly depends on symptomatic treatment.

Hepatitis C virus (referred as "HCV" hereinafter) is a virus of the flaviviridae family which has a membrane. HCV genome is single stranded (+)-RNA of 9.5 kb in length and express polyprotein comprising of 3010 amino acids. The HCV polyprotein is cleaved co- and post translationally by cellular and viral protease to yield 3 structural proteins and 6 nonstructural proteins. 5'- and 3'-terminus of the HCV genome contain untranslated region (UTR), which highly conserved nucleotide sequence of all most genotype. Recently, it is known that 5'-UTR is a 330~341 nucleotide sequences and 3'-UTR includes 98 nucleotides at the back of poly A, termed to X region which might be played a role of RNA replication and post-translation of virus. Amino end part of HCV genome produces structural proteins Core, E1 and E2 and the other part comprise of non-structural protein. The core is the main structural component of the viral capsid and E1 and E2 comprises of a outer protein. These proteins are cleaved by signal peptidase in endoplasmic reticulum. Serin-type protease NS3 and cofactor NS4A are responsible for the cleavage of nonstructural protein. NS5B protein is a RNA-dependant RNA polymerase. This protein is the most importance enzyme involved in the regulation of HCV replication.

It is reported that an infection by HCV is generated from a blood transfusion and community-acquired infection. Approximately 70% of HCV infected individuals will develop chronic hepatitis, of which 20% will progress to severe chonic liver disease within 5 years. Such higher progression rate, rarely in RNA virus, shows that HCV is a major cause of generating liver cancer. Mechanism studies of the continuous infection of HCV have not been reported. HCV test is therefore carried out in all blood and the infection opportunity by the blood transfusion is remarkably decreased. But, HCV infection presents a major public health problem worldwide because the community-acquired HCV infection has not regulated yet.

From the view of retrospective studies, HCV infection uniformly distributes worldwide and 1.5–2% of the world's population is infected. Compared to HBV, HCV infection is generally developed in chronic hepatitis and has a high probability of progression to liver cirrhosis and liver cancer. Hepatitis C virus that belongs to completely different family cannot be inhibited using B-type vaccine and treatment with α-interferon. That treatment have not shown a remarkable antiviral effect owing to their variable genotype.

Since HCV was discovered in 1987, there has been attempted a lot of research, but remarkably effective drug has not yet developed. Interferon is the unique choice for the treatment so far, but it has confirmed that its medical care rate is less than 30%, HCV is recurred after cessation of its treatment and several interferon-resistant mutant virus generates. So far, there are not characteristic antiviral agents with proliferation inhibitory activity against HCV.

Meanwhile, AIDS is a disease inducing dramatic decrease in immune function in the body cells and causing various symptoms of infection rarely seen in normal human beings, which spread to the whole body. Human immunodeficiency virus (HIV; referred as "HIV" hereinafter) responsible for AIDS is known to mainly attack helper T cells, which is one of the T cells with regulatory function in the immune system. When helper T cells are infected with HIV virus and undergo necrosis, human immune system cannot function properly. Impairment in immune function subsequently results in fatal infection and development of malignant tumor. Since AIDS patient has been found in USA in 1981 for the first time, the number increased to more than 830,000 patients in 187 countries in 1993 (WHO 1993 report). WHO predicted that 30 to 40 million more people would be infected with HIV by the year 2000 and 10 to 20 million of them would develop the disease.

At the present time, drugs controlling proliferation of HIV have been most widely used for the treatment of AIDS. Of these, Zidovudine, which had been named Azidothymidine previously, is a drug developed in 1987. Didanosine was developed in 1991 as an alternative medicine for AIDS patients when Zidovudine was either ineffective or could not be used due to side effects. In addition, Zalcitabine was approved for concurrent use with Zidovudine in 1992. These drugs alleviate symptoms, slow down progression of the disease in the infected individuals to full-blown AIDS, and somewhat extend life span in the patients. These drugs, however, are not able to cure the patients completely and often develop problems such as resistance and side effects.

In light of these problems, we, inventors of the present invention, tried to develop therapeutics to treat hepatitis B with little chance of toxicity, side effects, and development of resistant viral strains. We found the compounds with excellent antiviral effect against HBV; synthesized novel 6-methylnicotinamide derivatives represented in formula 1 and completed the invention by showing their dramatic inhibitory effect on proliferation of HIV and HCV as well as of HBV.

It is an object of this invention to provide novel 6-methylnicotinamide derivatives, their pharmaceutically acceptable salts, and their preparation.

It is a further object of this invention to provide a pharmaceutical compositions containing said derivatives with cost effectiveness and little chance of side effects, as a therapeutic agent as well as a preventive agent for hepatitis B, hepatitis C and acquired immune deficiency syndrome (AIDS).

DETAILED DESCRIPTION OF THE INVENTION

The present invention provides novel 6-methylnicotinamide derivatives represented by following formula 1 and their pharmaceutically acceptable salts.

Formula 1

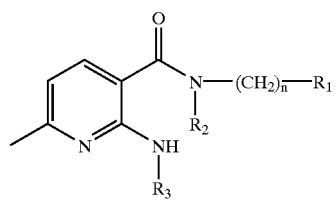

wherein,

R$_1$ is hydroxy group; straight or branched C$_1$~C$_5$ alkyl group; C$_3$~C$_6$ cycloalkyl group which is unsubstituted or substituted with hydroxy group, C$_2$~C$_6$ dialkylamino group; saturated or unsaturated 5 or 6 membered heterocyclic compounds containing 1 to 2 heteroatoms selected from N, O and S which may be unsubstituted or substituted with C$_1$~C$_3$ alkyl group; or

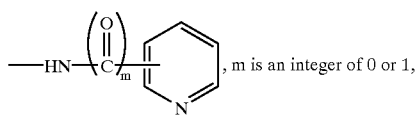, m is an integer of 0 or 1, $R_2$ is H or $C_1$~$C_4$ alkyl group;

or $R_1$ and $R_2$ are joined to form a 5- and 6-membered heterocyclic ring containing 1 to 2 heteroatoms selected from N, O and S, n is an integer from 0 to 4, $R_3$ is 5-indazole or 6-indazole More preferably, wherein, $R_1$ is hydroxyl, methyl, isopropyl, t-butyl, cyclo propyl, 4-hydroxyl-1-cyclohexyl, dimethyl amino, 4-morphorinyl, 1-piperidinyl, 4-methyl-1-piperazinyl, 2-pyridyl, 3-pyridyl, 1-imidazolyl, 2-pyridylamino or 3-pyridylcarbonyl amino, $R_2$ is H, n is an integer from 0 to 3.

More preferable compounds in accordance with the present invention are as follows;

1) 2-(1H-5-indazolylamino)-N-isopropyl-6-methylnicotinamide, (compound of example 1),
2) 2-(1H-5-indazolylamino)-6-methyl-N-(4-morpholinyl)nicotinamide, (compound of example 2),
3) N-(trans-4-hydroxy-1-cyclohexyl)-2-(1H-5-indazolylamono)-6-methylnicotinamide, (compound of example 3),
4) 2-(1H-5-indazolylamino)-6-methyl-N-(3-pyridyl)nicotinamide, (compound of example 4),
5) 2-(1H-5-indazolylamino)-6-methyl-N-(3-pyridylmethyl)nicotinamide, (compound of example 5),
6) 2-(1H-5-indazolylamino)-6-methyl-N-(2-pyridylethyl)nicotinamide, (compound of example 6),
7) 2-(1H-6-indazolylamino)-6-methyl-N-methylnicotinamide, (compound of example 7),
8) 2-(1H-6-indazolylamino)-N-isopropyl-6-methylnicotinamide, (compound of example 8),
9) N-(t-butyl)-2-(1H-6-indazolylamino)-6-methylnicotinamide, (compound of example 9),
10) N-(2-hydroxyethyl)-2-(1H-6-indazolylamino)-6-methylnicotinamide, (compound of example 10),
11) N-cyclopropyl-2-(1H-6-indazolylamino)-6-methylnicotinamide, (compound of example 11),
12) N-[2-(dimethylamino)ethyl]-2-(1H-6-indazolylamino)-6-methylnicotinamide, (compound of example 12),
13) N-[2-(diethylamino)ethyl]-2-(1H-6-indazolylamino)-6-methylnicotinamide, (compound of example 13),
14) 2-(1H-6-indazolylamino)-6-methyl-N-[2-(4-morpholinyl)ethyl]nicotinamide, (compound of example 14),
15) 2-(1H-6-indazolylamino)-6-methyl-N-[2-(1-piperidinyl)ethyl]nicotinamide, (compound of example 15),
16) 2-(1H-6-indazolylamino)-6-methyl-N-(4-morpholinyl)nicotinamide, (compound of example 16),
17) 2-(1H-6-indazolylamino)-6-methyl-N-(4-methyl-1-piperazinyl)nicotinamide, (compound of example 17),
18) 2-(1H-6-indazolylamino)-6-methyl-N-(3-pyridyl)nicotinamide, (compound of example 18),
19) 2-(1H-6-indazolylamino)-6-methyl-N-(3-pyridylmethyl)nicotinamide, (compound of example 19),
20) N-[3-(1H-1-imidazolyl)propyl]-2-(1H-6-indazolylamino)-6-methylnicotinamide, (compound of example 20),
21) 2-(1H-6-indazolylamino)-6-methyl-N-(2-pyridyl)-3-pyridinecarbohydrazide, (compound of example 21),
22) 2-(1H-6-indazolylamino)-6-methyl-N-(3-pyridylcarbonyl)-3-pyridinecarbohydrazide, (compound of example 22),
23) 2-(1H-6-indazolylamino)-6-methyl-3-(4-morpholinylcarbonyl)pyridine, (compound of example 23).

The compounds according to the present invention have an inhibitory effect on proliferation of HIV as well as HBV, HCV since containing 5-indazolylamino or 6-indazolylamino as a substituent of 6-methylnicotinamide derivatives.

The compounds represented by formula 1 of the present invention may be utilized in the form of salts and the acid addition salts prepared by adding pharmaceutically acceptable free acids are useful. Compounds of formula 1 may be changed to the corresponding acid addition salts according to the general practices in this field. Both inorganic and organic acids may be used as free acids in this case. Among inorganic acids, hydrochloric acid, hydrobromic acid, sulfuric acid, or phosphoric acid may be used. Among organic acids, citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, galacturonic acid, embonic acid, glutamic acid or aspartic acid may be used.

The present invention also provides a process for preparing 6-methylnicotinamide derivatives of formula 1, represented by scheme 1 as follows:

Scheme 1

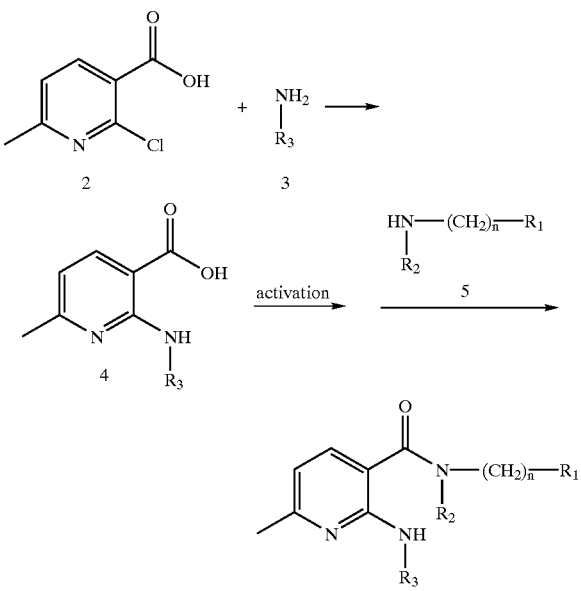

wherein, $R_1$, $R_2$, $R_3$ and n are as defined in formula 1.

The process for preparing in the present invention comprises the following steps of:

1) preparing of 6-methylnicotinic acid derivatives (4) substituted with aminoindazole by heating and reacting 2-chloro-6-methylnicotinic acid (2) with 5-aminoindazole or 6-aminoindazole (3) in the presence of a base (step 1); and,
2) preparing of 6-methylnicotinamide derivatives of formula 1 by activating the 6-methylnicotinic derivatives (4) prepared in step 1, and then reacting the compounds of formula 4 with amine compound (5) (step 2).

A detail description will be stepwise given of the method for preparing 6-methylnicotinamide derivatives of the present invention.

Chemical reagents used as starting and reaction materials in the step 1 and 2 of the scheme 1, namely, 2-chloro-6-methylnicotinic acid (2), 5-aminoindazole (3), 6-aminoindazole (3) and amine compound (5), are commercially available and may be purchased.

The amine compound (5) in the step 2 is also used to introduce a constituent ($R-NR_2-(CH_2)_n-R_1$) into the desired compound of formula 1 and an appropriate amine compound should be selected depending on the substituent desired, which can be easily done by one with general knowledge in the technical field.

In the step 1, it is preferably used tertiary organic base having weak basicity such as pyridine, picoline, lutidine, N,N-dimethylaniline, 4-dimethylaminopyridine, as a base.

In the step 2, compounds of the formula 1 is prepared by reacting with amine compound (5) after activating 6-methylnicotinic acid derivatives (4) obtained by the step 1.

In activating process, 6-methylnicotinic acid derivatives are activated to highly reactive acid chloride compounds by adding a bit excess thionyl chloride to 6-methylnicotinic acid derivatives (4), subsequently heating, or, by Vilsmeier reagent prepared by heating thionyl chloride and N,N-dimethylformamide.

For a solvent, a protonic solvent is preferable, for example, a single or a mixture of solvents selected from chloroform, methylene chloride, acetonitrile, tetrahydrofuran and ether.

The reaction temperature is preferably 0~20° C.

Furthermore, the present invention provides the pharmaceutical compositions of therapeutics comprising 6-methylnicotinamide derivatives or their pharmaceutically acceptable salts of formula 1 as effective ingredients to prevent and treat hepatitis B.

The present invention also provides the pharmaceutical compositions of therapeutics, comprising 6-methylnicotinamide derivatives or their pharmaceutically acceptable salts of formula 1 as effective ingredients to prevent and treat hepatitis C.

An inhibitor of RNA-dependant RNA-polymerase in the HCV, can essentially inhibit on HCV proliferation, and the compounds of the present invention is therefore expected to be useful for therapeutic agents on Hepatitis C with low toxicity since the RNA-dependant RNA-polymerase is not detected yet in human body cell.

6-methylnicotinamide derivatives of formula 1 in present invention have an inhibitory effect on proliferation of both HIV and HBV because they interfere with removal of RNA strand from RNA-DNA hybrid formed during the reverse transcription of viral RNA to DNA, which is a common step in the replication mechanism of the two viruses.

Therefore, the present invention also provides the pharmaceutical compositions of therapeutics for preventing and treating AIDS, which comprise 6-methylnicotinamide derivatives or their pharmaceutically acceptable salts of formula 1 as effective ingredients.

Compounds of formula 1 may be taken orally as well as through other routes in clinical uses; for example, it may be administered intravenously, subcutaneously, intraperitoneally, locally and in the form of general drugs.

For clinical use of drugs with the pharmaceutical compositions of the present invention, compounds of formula 1 may be mixed with pharmaceutically acceptable excipients and made into various pharmaceutically acceptable forms; for example, to tablets, capsules, trochese, solutions, suspensions for oral administration; infection solutions, suspensions, and dried powder to be mixed with distilled water for the formulation of instant injection solution.

Effective dosage for compound of formula 1 is generally 10~500 mg/kg, preferably 50~300 mg/kg for adults, which may be divided into several doses, preferably into 1~6 doses per day if deemed appropriate by a doctor or a pharmacist.

Hereinafter the present invention describes in more detail. However, it will be appreciated that those skilled in the art, on consideration of this disclosure, may make modifications and improvements within the spirit and scope of the present invention.

EXAMPLE

Preparation Example 1

Preparation of2-(1H-5-Indazolylamino)-6-methylnicotinic Acid

To the solution of 2-chloro-6-methylnicotinic acid 10 g and 5-aminoindazole (8.6 g) in methanol 70 ml was added pyridine 10 ml, and then the solution was reacted at 40~50° C. for 3 days. The reaction mixture was cooled, added $H_2O$ 35 ml slowly at 20° C., and then stirred for 2 hr. The reaction mixture was filtered to obtaining a solid, and the solid was washed with 50% methaol 15 ml to obtaining a solid product. The desired compound (13 g, yield 83%) was obtained by drying of the solid product at 40~50° C. in vacuo.

m.p. : 252~254° C.

$^1$H-NMR (DMSO-$d_6$), ppm: δ 2.40 (s, 3H), 6.66 (d, 1H), 7.41 (m, 2H), 7.96 (d, 1H), 8.09 (d, 1H), 8.31 (q, 1H), 10.42 (s, 1H), 13.13 (br S, 2H)

Preparation Example 2

Preparation of 2-(1H-6-Indazolylamino)-6-methylnicotinic Acid

To the solution of 2-chloro-6-methylnicotinic acid 10 g and 6-aminoindazole 8.6 g in methanol 100 ml was added pyridine 9.5 ml, and then the solution was refluxed for 3 days. The reaction mixture was cooled, added H20 30 ml slowly at 20° C., and then stirred for 2 hr. The reaction mixture was filtered and the obtained solid was washed with methaol 20 ml. The desired compound (13.3 g, yield 85%) was obtained by drying of the solid product at 40~50° C. in vacuo.

m.p.: 273–274° C. $^1$H-NMR (DMSO-$d_6$), ppm: δ 2.49 (s, 3H), 6.75 (d, 1H), 7.01 (d, 1H), 7.65 (m, 1H), 7.93 (s, 1H), 8.14 (m, 1H), 8.53 (s, 1H), 10.70 (s, 1H), 13.13 (br s, 2H)

Example 1

Preparation of 2-(1H-5-Indazolylamino)-N-isopropyl-6-methylnicotinamide

To the solution of methylene chloride (120 ml) was added N,N-dimethylformamide (2.3 ml) and thionyl chloride (2.7 ml) and the solution was refluxed for 2 hr. 2-(1H-5-indazolylamino)-6-methylnicotinic acid 4 g obtained by preparation example 1 was added to the solution and the reaction mixture was refluxed for 2 hr. The reaction mixture was cooled and isopropyl amine 6 ml was slowly added.

After stirring for 1 hr, the reaction mixture was concentrated under reduced pressure. The residue was diluted with methanol 50 ml and H$_2$O 50 ml and 3N—NaOH aqueous solution was added to adjust to pH=9~10. The solution was stirred at 20° C. for 30 min. and filtered to the solid. The solid was recrystallized with chloroform: isopropyl ether=1:10 to obtain the desired compound (3.6 g, yield 78%).

m.p.: 203–206° C. $^1$H-NMR (DMSO-d$_6$), ppm: δ 1.17 (d, 6H), 2.40 (s, 3H), 4.12 (m, 1H), 6.65 (d, 1H), 7.35 (d, 1H), 7.43 (d, 1H), 7.96 (s, 1H), 8.00 (d, 1H), 8.34 (d, 2H), 11.01 (s, 1H), 12.89 (s, 1H)

Example 2

Preparation of 2-(1H-5-Indazolylamino)-6-methyl-N-(4-morpholinyl)nicotinamide

To the solution of methylene chloride 30 ml was added N,N-dimethylformamide 0.34 ml and thionyl chloride 0.4 ml and the solution was refluxed for 2 hr. 2-(1H-5-indazolylamino)-6-methylnicotinic acid 0.6 g obtained by preparation example 1 was added to the solution and the reaction mixture was refluxed for 2 hr. The reaction mixture was cooled and 4-aminomorpholine 1 ml was slowly added. After stirring for 1 hr, the reaction mixture was concentrated under reduced pressure. The residue was diluted with H$_2$O 20 ml and 3N—NaOH aqueous solution was added to adjust to pH=9~10. The solution was extracted with chloroform 30 ml. The organic layer was separated, concentrated under reduced pressure and the concentrate was purified by column chromatography (chloroform: isopropanol=10:1 (v/v)), and then recrystallized with ether to obtain the desired compound (0.45 g, yield 57%).

m.p.: 257~260° C. $^1$H-NMR (DMSO-d$_6$), ppm: δ 2.40 (s, 3H), 2.87 (br s, 4H), 3.66 (br s, 4H), 6.65 (d, 1H), 7.35 (d, 1H), 7.44 (d, 1H), 7.91 (d, 1H), 7.97 (s, 1H), 8.33 (s, 1H), 9.63 (s, 1H), 10.66 (s, 1H), 12.90 (s, 1H)

Example 3

Preparation of N-(Trans-4-hydroxy-1-cyclohexyl)-2-(1H-5-indazolylamino)-6-methylnicotinamide To the solution of N,N-dimethylformamide 0.23 ml in methylene chloride 20 ml was added thionyl chloride 0.27 ml, the solution was refluxed for 2 hr. 2-(1H-5-indazolylamino)-6-methylnicotinic acid 0.4 g obtained by preparation example 1 was added and the solution was refluxed for 2 hr. The reaction mixture was cooled and to the reaction mixture were added trans-4-aminocyclohexanol chloride (salt) 0.7 g and triethylamine 0.8 ml slowly at 0–5° C. and then the mixture was stirred for 1 hr. The reaction mixture was concentrated under reduced pressure and the residue was diluted with methanol 7 ml and H$_2$O 12 ml and 3N—NaOH aqueous solution was added to adjust to pH=10. After stirring at 20° C. for 30 min, the mixture was filtered to obtain the solid product. The solid product was washed with H$_2$O, recrystallized with methanol and methylene chloride to obtain the desired compound (0.35 g, yield 64%).

m.p.: >280° C. $^1$H-NMR (DMSO-d$_6$), ppm: δ 1.19 (m, 2H), 1.32 (m, 2H), 1.80 (m, 4H), 2.39 (s, 3H), 3.38 (d, 1H), 3.86 (br s, 1H), 4.58 (d, 1H), 6.64 (q, 1H), 7.35 (d, 1H), 7.43 (m, 1H), 7.96 (m, 2H), 8.28(t, 2H), 10.96 (d, 1H), 12.90 (s, 1H)

Example 4

Preparation of 2-(1~1H-5-Indazolylamino)-6-methyl-N-(3-pyridyl)nicotinamide

The desired compound (yield 53%) was obtained by performing at the same manner as example 2, except for using 3-aminopyridine instead of 4-aminomorpholine.

m.p.: 237~240° C. $^1$H-NMR (DMSO-d$_6$), ppm: δ 2.44 (s, 3H), 6.76 (d, 2H), 7.39 (m, 3H), 7.98 (s, 1H), 8.12 (d, 1H), 8.18 (q, 1H), 8.31(t, 2H), 8.87 (s, 1H), 10.47 (s, 1H), 12.92 (s, 1H)

Example 5

Preparation of 2-(1H-5-Indazolylamino)-6-methyl-N-(3-pyridylmethyl)nicotinamide

The desired compound was obtained at the same manner as example 1, except for using 3-(aminomethyl)pyridine instead of isopropylamine.

m.p.: 95~97° C. $^1$H-NMR (DMSO-d$_6$), ppm: δ 2.40 (s, 3H), 4.50 (br s, 2H), 6.69 (d, 1H), 7.30 (m, 3H), 7.74 (s, 1H), 7.96 (s, 1H), 8.05 (d, 1H), 8.32 (s, 1H), 8.46 (s, 1H), 8.57 (s, 1H), 9.23 (s, 1H), 10.94 (s, 1H), 12.93 (s, 1H)

Example 6

Preparation of 2-(1H5-Indazolylamino)-6-methyl-N-(2-pyridylethyl)nicotinamide

The desired compound (yield 73%) was synthesized at the same manner as the example 2, except for using 2-(2-aminoethyl)pyridine instead of 4-aminomorpholine. The crude product was purified by column chromatograpy (hexane:ethyl acetate:methanol=5:5:1(v/v)) and recrystallized with isopropyl ether.

m.p.: 98~99° C. $^1$H-NMR (DMSO-d$_6$), ppm 6 2.40 (s, 3H), 3.02 (br s, 2H), 3.62 (br s, 2H), 6.65 (d, 1H), 7.20 (d, 1H), 7.28 (d, 1H), 7.36 (d, 1H), 7.44 (d, 1H), 7.68(t, 1H), 7.92 (d, 1H), 7.94 (s, 1H), 8.33 (s, 1H), 8.49 (s, 1H), 8.74 (s, 1H), 10.96 (s, 1H), 12.90 (s, 1H)

Example 7

Preparation of 2-(1H-6-Indazolylamino)-6-methyl-N-methylnicotinamide

To the solution of 2-(1H-6-indazolylamino)-6-methylnicotinic acid 0.9 g obtained by preparation example 2 in acetonitrile 30 ml was added thionyl chloride 0.75 ml slowly. After stirring at 70° C. for 1 hr, the mixture was cooled, methylamine (40% methanol solution) 3 ml was slowly added at 0~5° C. and the mixture was reacted for 30 min. The reaction mixture was diluted with H$_2$O 30 ml and acetonitrile was removed under reduced pressure. The solution was extracted with chloroform 50 ml. The organic layer was separated, concentrated under reduced pressure and residue was recrystallized with methylene chloride: ether= 2:1 (v/v) to obtain the desired compound (0.67 g, yield 71%).

m.p.: 210~211° C. $^1$H-NMR (DMSO-d$_6$), ppm: δ 2.49 (s, 3H), 2.81 (s, 3H), 6.76(d , 1H), 6.95 (d, 1H), 7.62 (d, H), 7.91 (s, 1H), 8.01(dd, 1H), 8.53 (s, 1H), 8.69 (br s, 1H), 11.36 (s, 1H), 12.81 (br s 1H)

Example 8

Preparation of 2-(1H-6-Indazolylamino)-N-isopropyl-6-methylnicotinamide

To the solution of 2-(1H-6-indazolylamino)-6-methylnicotinic acid 0.9 g obtained by preparation example 2 in acetonitrile 30 ml was added thionyl chloride 0.75 ml slowly. After stirring at 70° C. for 1 hr, the solution was cooled. To the reaction mixture was added isopropylamine 2.5 ml slowly at 0~5° C. and the mixture was reacted for 30 min. The reaction mixture was diluted with H$_2$O 30 ml and then concentrated under reduced pressure. To the residue was added 3N—NaOH aqueous solution to adjust to pH=9~9.5, and the mixture was stirred for 1 hr and then filtered to obtain a solid product. The solid product was washed with H$_2$O, recrystallised with methylene chloride and ether 1:4 (v/v) to obtain the desired compound (0.78 g, yield 75%).

m.p.: 212–214° C. $^1$H-NMR (DMSO-d$_6$), ppm: δ 1.86 (m, 6H), 2.49 (s, 3H)), 4.15 (m, 1H), 6.76 (d, 1H)), 6.95 (d, 1H), 7.61(dd, 1H), 7.92 (s, 1H), 8.07(dd, 1H), 8.44 (br s, 1H), 8.53 (s, 1H), 11.31 (s, 1H), 12.86 (br s, 1H)

Example 9
Preparation of N-(t-butyl)-2-(1H-6-Indazolylamino)-6-methylnicotinamide To the solution of 2-(1H-6-indazolylamino)-6-methylnicotinic acid 1.0 g obtained by preparation example 2 in acetonitrile 30 ml was added thionyl chloride 0.83 ml slowly. The solution was reacted at 70° C. for 1 hr and t-butyl amine 3 ml was slowly added at 0~5° C. After stirring for 30 min., Methanol 30 ml was added to the reaction mixture at 20° C. and the mixture was filtered. The filterate concentrated under reduced pressure was diluted with methanol 5 ml and precipitated in $H_2O$ 30 ml. The mixture was stirred for 1 hr, filtered and washed with $H_2O$ 5 ml. The obtained solid product was purified by column chromatography (n-Hexane:ethyl acetate:methanol=10:5:1 (v/v)) to obtain the desired compound (0.75 g, yield 62%).

m.p.: 107~109° C. $^1$H-NMR (DMSO-$d_6$), ppm: δ 1.39 (s, 9H), 2.49 (s, 3H), 6.72 (d, 1H), 6.93 (d, 1H), 7.60 (d, 1H), 7.90 (s, 1H), 7.99 ((m, 2H), 8.48 (s, 1H), 11.04 (s, 1H), 12.78 (br s, 1H)

Example 10
Preparation of N-(2-Hydroxyethyl)-2-(1H-6-Indazolylamino)-6-methylnicotinamide The desired compound (yield 58%) was prepared at the same manner as example 9, except for using ethanol amine instead of t-butyl amine.

m.p.: 217~220° C. $^1$H-NMR (DMSO-$d_6$), ppm: δ 2.49 (s, 3H), 3.33 (m, 2H), 3.52 (m, 2H), 4.77 (br s, 1H), 6.75 (d, 1H), 6.93 (d, 1H), 7.60 (d, 1H), 7.90 (s, 1H), 8.06 (d, 1H), 8.52 (s, 1H), 8.67 (br s, 1H), 11.29 (s, 1H), 12.79 (br s, 1H)

Example 11
Preparation of N-cyclopropyl-2-(1H-6-Indazolylamino)-6-methylnicotinamide To the solution of 2-(1H-6-indazolylamino)-6-methylnicotinic acid 1.0 g obtained by preparation example 2 in acetonitrile 30 ml was added thionyl chloride 0.83 ml slowly. The solution was reacted at 70° C. for 1 hr and then cooled. To the reaction mixture was added cyclopropyl amine 2.3 ml slowly at 0~5° C. and the mixture was reacted for 30 min. The reaction mixture was diluted with methanol 10 ml and methylene chloride 10 ml and filtered to remove the undissolving inevitable impurity. The residue concentrated under reduced pressure, was dissolved in methanol 10 ml, added $H_2O$ 40 ml and 3N—NaOH aqueous solution 2 ml. After stirring for 1 hr, the mixture was filtered and then washed with $H_2O$. The obtained solid product was recrystallized with chloroform: ether=1:5 (v/v) to obtain the desired compound (0.79 g, yield 69%).

m.p.: 189–190° C. $^1$H-NMR (DMSO-$d_6$), ppm: δ 0.59 (m, 2H), 0.70 (m, 2H), 2.49 (s, 3H), 2.85 (m, 1H), 6.73 (d, 1H), 6.95 (d, 1H), 7.60 (d, 1H), 7.90 (s, 1H), 7.99 (d, 1H), 8.52 (s, 1H), 8.64 (br s, 1H), 11.31 (s, 1H), 12.80 (br s, 1H)

Example 12
Preparation of N-[2-(Dimethylamino)ethyl]-2-(1H-6-indazolylamino)-6-methylnicotinamide The desired compound (yield 66%) was obtained by performing at the same manner as example 9, except for using N,N-dimethylethylene diamine instead of t-butyl amine.

m.p.: 182–183° C. $^1$H-NMR (DMSO-$d_6$), ppm: δ 2.21 (s, 6H), 2.49 (s, 3H), 3.38 (m, 4H), 6.77 (d, 1H), 6.96 (d, 1H), 7.62 (d, 1H), 7.92 (s, 1H), 8.04 (d, 1H), 8.52 (s, 1H), 8.66 (br s, 1H), 11.29 (s, 1H), 12.81 (br s, 1H)

Example 13
Preparation of N-[2-(Diethylamino)ethyl]-2-(1H-6-indazolylamino)-6-methylnicotinamide The desired compound(yield 58%) was obtained by performing at the same manner as example 9, except for using N,N-diethylethylene diamine instead of t-butyl amine.

m.p.: 154~155° C. $^1$H-NMR (DMSO-$d_6$), ppm: δ 0.99 (m, 6H), 2.45~2.55 (m, 9H), 3.35 (m, 2H), 6.77 (d, 1H), 6.95 (d, 1H), 7.62 (d, 1H), 7.92 (s, 1H), 8.02 (d, 1H), 8.52 (s, 1H), 8.66 (br s, 1H), 11.28 (s, 1H), 12.82 (br s, 1H)

Example 14
Preparation of 2-(1H-6-Indazolylamino)-6-methyl-N-[2-(4-morpholinyl)ethyl]nicotinamide To the solution of 2-(1H-6-indazolylamino)-6-methylnicotinic acid 1.0 g obtained by preparation example 2 in acetonitrile 40 ml was added thionyl chloride 0.83 ml slowly and the solution was reacted at 70° C. for 1 hr. The reaction mixture was cooled and 4-(2-aminoethyl) morpholine 4.0 ml was slowly added at 0~5° C. After stirring for 30 min., the reaction mixture was filtered at 20° C. and washed with acetonitrile 5 ml to remove an undissolving inevitable impurity. The filterate concentrated under reduced pressure, was dissolved in methylene chloride 40 ml and washed with $NaCO_3$ aqueous solution and $H_2O$. The organic layer was concentrated under reduced pressure and recrystallized with chloroform: ether=1:3 (v/v) to obtain the desired compound (1.04 g, yield 73%).

m.p.: 165~168° C. $^1$H-NMR (DMSO-$d_6$), ppm: δ 2.42 (m, 4H), 2.49 (s, 3H), 3.33~3.42 (m, 4H), 3.57 (m, 4H), 6.77 (d, 1H), 6.95 (d, 1H), 7.62 (d, 1H), 7.92 (s, 1H), 8.03 (d, 1H), 8.52 (s, 1H), 8.66 (br s, 1H), 11.27 (s, 1H), 12.81 (br s, 1H)

Example 15
Preparation of 2-(1H-6-Indazolylamino)-6-methyl-N-[2-(1-piperidinyl)ethyl]nicotinamide The desired compound (yield 62%) was obtained by performing at the same manner as example 9, except for using 1-(2-aminoethyl)piperidine instead of t-butyl amine.

m.p.: 177~179° C. $^1$H-NMR (DMSO-$d_6$), ppm: δ 1.37 (m, 2H), 1.50 (m, 4H), 2.49 (m, 7H), 3.35 (m, 4H), 6.77 (d, 1H), 6.95 (d, 1H), 7.62 (d, 1H), 7.92 (s, 1H), 8.02 (d, 1H), 8.52 (s, 1H), 8.65 (br s, 1H), 11.27 (s, 1H), 12.81 (br s, 1H)

Example 16
Preparation of 2-(1H-6-Indazolylamino)-6-methyl-N-(4-morpholinyl)nicotinamide The desired compound (yield 70%) was prepared at the same manner as example 14, except for using 4-aminomorpholine instead of 4-(2-aminoethyl)morpholine. Then crude product was purified by recrystallization with ethyl acetate: hexane=1:1 (v/v).

m.p.: 265~268° C. $^1$H-NMR (DMSO-$d_6$), ppm: δ 2.48 (s, 3H), 2.88 (s, 4H), 3.67 (s, 4H), 6.75 (d, 1H), 6.95 (d, 1H), 7. 60 (d, 1H), 7.90 (s, 1H), 7.96 (d, 1H), 8.50 (s, 1H), 9.69 (br s, 1H), 10.93 (s, 1H), 12.80 (br s, 1H)

Example 17
Preparation of 2-(1H-6-Indazolylamino)-6-methyl-N-(4-methyl-i-piperazinyl)nicotinamide The desired compound (yield 67%) was obtained by performing at the same manner as example 9, except for using 1-amino-4-methylpiperazine instead of t-butyl amine.

m.p.: 263~265° C. $^1$H-NMR (DMSO-$d_6$), ppm: δ 2.20 (s, 3H), 2.49 (s, 4H), 2.89 (s, 4H), 3.36 (s, 3H), 6.76 (d, 1H), 6.98 (d, 1H), 7.63 (d, 1H), 7.92 (s, 1H), 7.98 (d, 1H), 8.52 (s, 1H), 9.62 (br s, 1H), 10.92 (s, 1H), 12.83 (br s, 1H)

Example 18
Preparation of 2-(1H-6-Indazolylamino)-6-methyl-N-(3-pyridyl)nicotinamide The desired compound (yield 51%) was prepared at the same manner as example 11, except for using 3-aminopyridine instead of cyclopropyl amine. Then crude product was purified by recrystallization with methylene chloride: ether=1:2 (v/v).

m.p.: >280° C. $^1$H-NMR (DMSO-$d_6$), ppm: δ 2.49 (s, 3H), 6.83 (d, 1H), 6.97 (d, 1H), 7.39(dd, 1H), 7.59 (d, 1H), 7.89 (s, 1H), 8.11 (d, 1H), 8.21 (d, 1H), 8.31 (m, 1H), 8.47 (s, 1H), 8.85 (d, 1H), 10.52 (br s, 1H), 10.68 (s, 1H), 12.81 (br s, 1H)

Example 19
Preparation of 2-(1H-6-Indazolylamino)-6-methyl-N-(3-pyridylmethyl)nicotinamide The desired compound (yield 58%) was prepared at the same manner as example 11, except for using 3-(aminomethyl)pyridine instead of cyclopropyl amine. Then crude product was purified by recrystallization with chloroform: isopropylether=1:2 (v/v).

m.p.: 170~172° C. $^1$H-NMR (DMSO-$d_6$), ppm: δ 2.49 (s, 3H), 4.52 (s, 2H), 6.78 (d, 1H), 6.94 (d, 1H), 7.37 (dd, 1H), 7.60 (d, 1H), 7.91 (s, 1H), 8.11 (d, 1H), 8.48 (d, 1H), 8.51 (s, 1H), 8.58 (s, 1H), 9.31 (br s, 1H), 11.24 (s, 1H), 12.81 (br s, 1H)

Example 20
Preparation of N-[3-(1H-1-Imidazolyl)propyl]-2-(1H-6-indazolylamino)-6-methylnicotinamide The desired compound (yield 65%) was prepared at the same manner as example 14, except for using 1-(3-aminopropyl)imidazole instead of 4-(2-aminoethyl) morpholine. Then crude product was purified by recrystallization with ethanol : isopropyl ether=1:3 (v/v).

m.p.: 203~205° C. $^1$H-NMR (DMSO-$d_6$), ppm: δ 1.99 (m, 2H), 2.49 (s, 3H), 3.34 (m, 2H), 4.04 (m, 2H), 6.78 (d, 1H), 6.89 (s, 1H), 6.95 (d, 1H), 7.22 (s, 1H), 7.61 (d, 1H), 7.67 (s, 1H), 7.91 (s, 1H), 8.05 (d, 1H), 8.53 (s, 1H), 8.73 (br s, 1H), 11.24 (s, 1H), 12.81 (br s, 1H)

Example 21
Preparation of 2-(1H-6-Indazolylamino)-6-methyl-N-(2-pyridyl)-3-pyridinecabohydrazide To the solution of 2-(1H-6-indazolylamino)-6-methylnicotinic acid 1.0 g obtained by preparation example 2 in acetonitrile 30 ml was added thionyl chloride 0.83 ml slowly. After stirring at 70° C. for 1 hr, the reaction mixture was cooled. Then 2-hydrazinopyridine 2.7 g was slowly added at 0~5° C. and the mixture was stirred for 30 min. The reaction mixture was diluted with methanol 10 ml and methylene chloride 10 ml, stirred for 10 min., and then filtered. The filterate was concentrated under reduced pressure and the residue was dissolved in methanol 10 ml. To the solution were slowly added $H_2O$ 20 ml and 3N—NaOH aqueous solution a little to adjust to pH=8. The solution was stirred for 2 hr and filtered to obtain the solid. The filtered product was washed with $H_2O$: methanol=4:1 (v/v) and dried at 40~50° C. in vacuo to obtain the desired compound (1.03 g, yield 77%).

m.p.: 143~145° C. $^1$H-NMR (DMSO-$d_6$), ppm: δ 2.49 (s, 4H), 6.67~6.72 (m, 2H), 6.79 (d, 1H), 6.93 (d, 1H), 7.51~7.59 (m, 2H), 7.89 (s, 1H), 8.06 (d, 1H), 8.16 (m, 1H), 8.48 (s, 1H), 8.55 (br s, 1H), 10.54 (br s, 1H), 10.87 (s, 1H), 12.80 (br s, 1H)

Example 22
Preparation of 2-(1H-6-Indazolylamino)-6-methyl-N-(3-pyridylcarbonyl)-3-pyridinecarbohydrazide The desired compound (yield 69%) was obtained by performing at the same manner as example 21, except for using nicotinic hydrazide instead of 2-hydrazinopyridine.

m.p.: 244~246° C. $^1$H-NMR (DMSO-$d_6$), ppm: δ 2.49 (s, 3H), 6.83 (d, 1H), 6.98 (d, 1H), 7.60 (m, 2H), 7.91 (s, 1H), 8.15 (d, 1H), 8.28 (d, 1H), 8.52 (s, 1H), 8.79 (d, 1H), 9.09 (s, 1H), 10.79 10.84 (m, 3H), 12.83 (br s, 1H)

Example 23
Preparation of 2-(1H-6-Indazolylamino)-6-methyl-3-(4-morpholinylcarbonyl)pyridine The desired compound (yield 64%) was prepared at the same manner as example 14, except for using morpholine instead of 4-(2-aminoethyl)morpholine. Then crude product was purified by recrystallization with methylene chloride: n-hexane=1:1 (v/v).

m.p.: 103~104° C.

1H-NMR (DMSO-$d_6$), ppm: δ 2.49 (s, 3H), 3.33 (m, 4H), 3.57 (m, 4H), 6.76 (d, 1H), 7.12 (d, 1H), 7.53 (d, 1H), 7.58 (d, 1H), 7.89 (s, 1H), 8.20 (d, 1H), 8.63 (br s, 1H), 12.76 (br s, 1H)

Experiment 1
Inhibitory Effect on the in vitro Activities of HBV Polymerase in Reverse Transcription The following in vitro experiment was performed to determine the effect of the compounds of formula 1 on the activity of HBV polymerase during reverse transcription.

The present inventors submitted application for a patent concerning HBV polymerase genetically expressed in and separated from E. coli, the process of its preparation, and the method to measure the enzyme activities (KR 94-3918, KR 96-33998). In the present experiments HBV polymerase was used which had been expressed in E. coli as stated above.

The method used in the present invention to measure in vitro reverse transcribing activities of HBV polymerase is as follows. Basic principles are the same as those for ELISA, nucleotides with biotin- or digoxigenin- group are included as substrates and anti-DIG antibodies attached to peroxidase enzyme recognize the polymerized substrates.

To the wells coated with streptavidin, 20 μl of HBV polymerase, 20 μl of reaction mixture (10 μM each of DIG-UTP and Biotin-UTP, 46 mM Tris-HCl, 266 mM KCl, 27.5 mM $MgCl_2$, 9.2 mM DTT substrate/primer hybrid), and 20 μl of test compound (added to 1, 0.1, and 0.01 μl/ml) were added and allowed to react at 22° C. for 15 hrs. During this reaction, HBV polymerase catalyzes DNA synthesis, and digoxigenin and biotin attached to nucleotides form bonds to streptavidin coated on the bottom of wells. When the reaction was done, each well was washed with 250 μl of cleaning buffer (pH 7.0) for 30 seconds, which was repeated five times to remove remaining impurities. 200 μl of anti-DIG-POD antibody was added to each well and allowed to react for 1 hr at 37° C., and the wells were washed with cleaning buffer to remove impurities. 200 μl each of ABTS™, a substrate of peroxidase, was then added and allowed to react at room temperature for 30 min. Absorbancy was measured at 405 nm using ELISA reader.

The inhibitory effects in HBV polymerase activities for reverse transcription were calculated using the group without test compound as a control and the results are shown in Table 1 as follows.

TABLE 1

Inhibitory effect on the HBV polymerase activities in reverse transription

| | Inhibitory activity on HBV-RT (%) | | |
|---|---|---|---|
| Compound | 1 µg/ml | 0.1 µg/ml | 0.01 µg/ml |
| Example 1 | 78 | 49 | 30 |
| Example 2 | 88 | 57 | 42 |
| Example 3 | 80 | 61 | 53 |
| Example 4 | 92 | 64 | 50 |
| Example 5 | 65 | 43 | 37 |
| Example 6 | 84 | 55 | 40 |
| Example 7 | 70 | 50 | 21 |
| Example 8 | 78 | 54 | 23 |
| Example 9 | 65 | 48 | 20 |
| Example 10 | 89 | 62 | 48 |
| Example 11 | 84 | 54 | 32 |
| Example 12 | 86 | 60 | 49 |
| Example 13 | 54 | 45 | 15 |
| Example 14 | 91 | 68 | 52 |
| Example 15 | 87 | 57 | 12 |
| Example 16 | 78 | 51 | 35 |
| Example 17 | 86 | 56 | 24 |
| Example 18 | 69 | 40 | 18 |
| Example 19 | 76 | 48 | 32 |
| Example 20 | 88 | 59 | 47 |
| Example 21 | 86 | 50 | 30 |
| Example 22 | 85 | 54 | 26 |
| Example 23 | 62 | 40 | 12 |

As shown in Table 1, the compounds of the present invention have excellent inhibitory effects on the HBV polymerase activities and the maximum result showed 92% inhibition at the concentration of 1 µg/ml. Moreover, the compounds of the present invention are non-nucleoside compounds, so they are not expected to have problems such as toxicity and early appearance of resistant viruses as observed in the use of nucleosides and may be applied together with nucleoside compounds due to different mechanisms of action.

In summary, the compounds of the present invention effectively reduce the activities of HBV polymerase that plays the important role in the replication of HBV, and as the result, they could inhibit replication and proliferation of HBV and may be useful as a therapeutic agent for prevention and treatment of hepatitis B.

Experiment 2
Inhibitory Effect on the in vitro HCV Activity in RNA-dependant RNA-polymerase.

The following in vitro experiment was performed to determine inhibitory effects of compounds of formula 1 on the activity in RNA-dependant RNA-polymerase.

To test in vitro for HCV activity in RNA-dependant RNA-polymerase, the following experiment was carried out.

First, 10 µl of HCV NS5B (RNA-polymerase) and 25 µl of reaction buffer solution [Tris. Cl (pH 7.5) 0.1 M, NaCl 0.1 M, MgCl$_2$ 0.01 M, KCl 0.2 M, EDTA 0.002 M, DTT 0.05 M] were added to a well coated with streptavidin. 10 µl of reaction mixture containing poly A/UTP, as a RNA template-primer, DIG-UTP, biotin-UTP and UTP were added and subsequently test compounds prepared were also added at the final concentration of 10, 1 and 0.1 µg/ml. The mixture was allowed to react 22° C. for 1 hr. The inhibitory activity was measured in comparison with negative control without the test compounds. At this time, RNA was formed from RNA by the action of HCV polymerase, forming bonds with streptavidin coated on the bottom of wells due to dioxigenin and biotin attached to nucleotides. When the reaction was completed, each well was washed with 200 µl of washing buffer (pH 7.0) for 30 sec. three times to remove remaining impurities. 200 µl of anti-DIG-POD antibody was added to each well and allowed to react for 1 hr at 37° C., and the wells were washed with cleaning buffer to remove impurities. 200 µl of ABTS™, a substrate for peroxidase(POD), was added to each well, allowed to react at room temperature for 30 min., and absorbance at 405 nm was measured for each solution using ELISA reader.

The percentage of inhibition effect in the activity of HCV RNA polymerase, was calculated using the negative control without the test compounds and the results are represented in Table 2. as follows.

TABLE 2

Inhibitory effect on the HCV proliferation

| | Inhibition activity on HBV-RT (%) | | |
|---|---|---|---|
| Compound | 1 µg/ml | 0.1 µg/ml | 0.01 µg/ml |
| Example 1 | 59 | 38 | 12 |
| Example 2 | 83 | 54 | 40 |
| Example 3 | 90 | 61 | 46 |
| Example 4 | 63 | 41 | 24 |
| Example 5 | 52 | 37 | 10 |
| Example 6 | 81 | 55 | 37 |
| Example 7 | 65 | 52 | 15 |
| Example 8 | 60 | 47 | 27 |
| Example 12 | 82 | 68 | 43 |
| Example 14 | 74 | 53 | 35 |
| Example 16 | 90 | 67 | 54 |
| Example 17 | 65 | 42 | 31 |
| Example 18 | 63 | 43 | 15 |
| Example 19 | 65 | 47 | 32 |
| Example 20 | 59 | 42 | 16 |
| Example 21 | 85 | 58 | 20 |
| Example 22 | 55 | 35 | 20 |

As shown above in Table 2, it is found that the compounds of the present invention have excellent inhibitory effect on 90% inhibition at the concentration of 10 µ/ml and approximately 60% at 1 µ/ml. Consequently, the compounds of the present invention effectively reduce the activities of HCV RNA-polymerase that plays the important role in the replication of HCV, and as the result, they could inhibit replication and proliferation of HCV and may be useful as a therapeutic agent for prevention and treatment of hepatitis C. Moreover, it is expected that the compounds of the present invention, being non-nucleotides, do not have problems such as toxicity and early appearance of resistant strains observed in the use of nucleoside substrates, furthermore may be used together with them since the mechanism differs from that of nucleotide compounds.

Experiment 3
Inhibitory Effect on the in vitro HIV Enzyme Activities in Reverse Transcription The following in vitro experiments were done to determine the effect of compounds of formula 1 on the inhibitory effect of HIV enzyme activities in reverse transcription.

Non-radioactive reverse transcriptase assay kit (Boehringer Mannheim) was used in the measurement of in vitro transcriptase activities. 20 µl (40 ng) of HIV reverse transcriptase and 20 µl of reaction mixture containing matrix-primer hybrid poly(A)oligo(dT)$_{15}$, DIG (digoxigenin)-dUTP, biotin-dUTP, dTTP were added to wells coated with streptavidin, and the test compounds prepared were also added at the final concentrations of 0.1 and 1 µ/ml and allowed to react at 37° C. for 1 hr. At this time, DNA is formed from RNA by the action of HIV reverse transcriptase, forming bonds with streptavidin coated on the bottom of wells through digoxigenin and biotin moieties attached to nucleotides.

When the reaction was completed, each well was washed with 250 μl of washing buffer (pH 7.0) for 30 sec. five times to remove remaining impurities. 200 μl of anti-DIG-POD antigen was added to each well, then the mixture was allowed to react at 37° C. for 1 hr and washed as above to remove impurities. 200 μl of ABTS™, a substrate for peroxidase, was added to each well and the mixture was allowed to react at room temperature for 30 min. Absorbance at 405 nm was measured for each solution using ELISA reader to determine the inhibitory effect on the HIV reverse transcriptase activities. The percentage of inhibition in the activity of HIV reverse transcriptase was calculated using the group without test compound as control and the results are represented in Table 3.

TABLE 3

Inhibitory effect on the activity of HIV reverse transcriptase

| | Inhibition activity on HIV-RT (%) | |
|---|---|---|
| Compound | 1 μg/ml | 0.1 μg/ml |
| Example 1 | 75 | 42 |
| Example 2 | 84 | 49 |
| Example 3 | 80 | 51 |
| Example 4 | 64 | 40 |
| Example 5 | 69 | 38 |
| Example 6 | 77 | 45 |
| Example 8 | 65 | 28 |
| Example 11 | 82 | 45 |
| Example 14 | 70 | 41 |
| Example 15 | 78 | 43 |
| Example 17 | 84 | 50 |
| Example 20 | 88 | 47 |
| Example 21 | 75 | 49 |

As shown above in Table 3, it is found that the compounds of the present invention have excellent inhibitory effect on the activities of HIV reverse transcriptase, having more than up to 80% inhibition at the concentration of 1 μg/ml, and approximately 50% at 0.1 μg/ml. Consequently, the compounds of the present invention effectively reduce the activities of HIV reverse transcriptase that plays the important role in the replication of HIV, and as the result, they could inhibit replication and proliferation of HIV and may be useful as a therapeutic agent for prevention and treatment of AIDS.

Moreover, it is expected that compounds of the present invention, being non-nucleosidic, do not have problems such as toxicity and early development of resistant virus strains observed in the use of nucleotide substances. Furthermore, The compounds of the present invention may be used together with nucleoside compounds since the former act on allosteric binding pockets while the latter act in the domain of polymerase activities.

Experiment 4
Cytotoxicity Test

To determine if compounds of formula 1 exhibit cytotoxicity, in vitro tests were carried out using HepG2 cells with MTT analysis method as generally known.

As a result, all of the compounds used in the experiments have higher than 100 μg/ml for $CC_{50}$ and are considered to have little cytotoxicity.

Experiment 5
Acute Toxicity in Rats Tested via Oral Administration

The following experiments were performed to see if compounds of formula 1 have acute toxicity in rats.

1) The Compounds Obtained from the Example 1~6

6-week old SPF SD line rats were used in the tests for acute toxicity. The compounds in the examples of 1–6 were suspended in 0.5% methylcellulose solution and orally administered once to 6 rats per group at the dosage of 2 g/kg/15 ml. Death, clinical symptoms, and weight change in rats were observed. Hematological tests and biochemical tests of blood were performed and any abnormal signs in the gastrointestinal organs of chest and abdomen were checked with eyes during autopsy. The results showed that the test compounds did not cause any specific clinical symptoms or death in rats and no change was observed in hematological tests, weight change, blood tests, biochemical tests of blood, and autopsy. As a results, the compounds of the example 1–6 used in this experiment, are evaluated to be safe substances since they do not cause any toxic change in rats up to the level of 2 g/kg and the $LD_{50}$ values are much greater than 2 g/kg in rats.

2) The Compounds Obtained from the Example 7~23

Acute toxicity was carried out through oral administration once to 6-week old SPF SD line rats per group at the dosage of 3 g/kg/15 ml, as a result, the compounds of the example 7~23 were considered to be safe since they do not cause any toxic change in rats up to the level of 3 g/kg , the $LD_{50}$ values are much greater than 3 g/kg in rats.

INDUSTRIAL APPLICABILITY

As described above, novel 6-methylnicotinamide derivatives represented by formula 1 of the present invention have the dramatic inhibitory effect on proliferation of HBV, HCV and HIV with little side effect and may be useful as therapeutic agents for prevention and treatment of hepatitis B and C, and AIDS. Moreover, it is expected that compounds of the present invention, being non-nucleosidic, do not have problems such as toxicity and early development of resistant virus strains observed by nucleoside substances. Furthermore, compounds of the present invention may be used together with nucleoside compounds since the former seem to act on allosteric binding pockets while the latter work in the domain of polymerase activities.

What is claimed is:

1. 6-methylnicotinamide derivatives of formula 1 or their pharmaceutically acceptable salts:

Formula 1

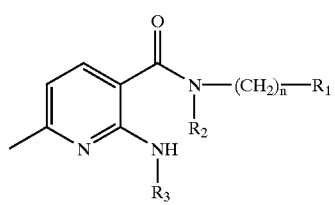

wherein, $R_1$ is hydroxy group; straight or branched $C_1$~$C_5$ alkyl group; $C_3$~$C_6$ cycloalkyl group which is unsubstituted or substituted with hydroxy group, $C_2$~$C_6$ dialkylamino group; saturated or unsaturated 5 or 6 membered heterocyclic compounds containing 1 to 2 heteroatoms selected from N, O and S which may be unsubstituted or substituted with $C_1$~$C_3$ alkyl group; or

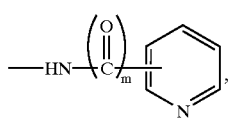

m is an integer of 0 or 1,
$R_2$ is H or $C_1$~$C_4$ alkyl group;
or $R_1$ and $R_2$ are joined to form a 5- and 6-membered heterocyclic ring containing 1 to 2 heteroatoms selected from N, O and S,
n is an integer from 0 to 4,
$R_3$ is 5-indazole or 6-indazole.

2. The 6-methylnicotinamide derivatives or their pharmaceutically acceptable salts according to claim 1, wherein, $R_1$ is hydroxy, methyl, isopropyl, t-butyl, cyclopropyl, 4-hydroxy-1-cyclohexyl, dimethylamino, 4-morpholinyl, 1-piperidinyl, 4-methyl-1-piperazinyl, 2-pyridyl, 3-pyridyl, 1-imidazolyl, 2-pyridylamino, or 3-pyridylcarbonylamino group;

$R_2$ is H; and
n is an integer from 0 to 3.

3. The 6-methylnicotinamide derivatives or their pharmaceutically acceptable salts according to claim 1, wherein the 6-methylnicotinamide derivatives represented by formula 1 are selected from the group consisting of:

1) 2-(1H-5-indazolylamino)-N-isopropyl-6-methylnicotinamide,
2) 2-(1H-5-indazolylamino)-6-methyl-N-(4-morpholinyl)nicotinamide,
3) N-(trans-4-hydroxy-1-cyclohexyl)-2-(1H-5-indazolylamino)-6-methylnicotinamide,
4) 2-(1H-5-indazolylamino)-6-methyl-N-(3-pyridyl)nicotinamide,
5) 2-(1H-5-indazolylamino)-6-methyl-N-(3-pyridylmethyl)nicotinamide,
6) 2-(1H-5-indazolylamino)-6-methyl-N-(2-pyridylethyl)nicotinamide,
7) 2-(1H-6-indazolylamino)-6-methyl-N-methylnicotinamide,
8) 2-(1H-6-indazolylamino)-N-isopropyl-6-methylnicotinamide,
9) N-(t-butyl)-2-(1H-6-indazolylamino)-6-methylnicotinamide,
10) N-(2-hydroxyethyl)-2-(1H-6-indazolylamino)-6-methylnicotinamide,
11) N-cyclopropyl-2-(1H-6-indazolylamino)-6-methylnicotinamide,
12) N-[2-(dimethylamino)ethyl]-2-(1H-6-indazolylamino)-6-methylnicotinamide,
13) N-[2-(diethylamino)ethyl]-2-(1H-6-indazolylamino)-6-methylnicotinamide,
14) 2-(1H-6-indazolylamino)-6-methyl-N-[2-(4-morpholinyl)ethyl]nicotinamide,
15) 2-(1H-6-indazolylamino)-6-methyl-N-[2-(1-piperidinyl)ethyl]nicotinamide,
16) 2-(1H-6-indazolylamino)-6-methyl-N-(4-morpholinyl)nicotinamide,
17) 2-(1H-6-indazolylamino)-6-methyl-N-(4-methyl-1-piperazinyl)nicotinamide,
18) 2-(1H-6-4indazolylamino)-6-methyl-N-(3-pyridyl)nicotinamide,
19) 2-(1H-6-indazolylamino)-6-methyl-N-(3-pyridylmethyl)nicotinamide,
20) N-[3-(1H-1-imidazolyl)propyl]-2-(1H-6-indazolylamino)-6-methylnicotinamide,
21) 2-(1H-6-indazolylamino)-6-methyl-N-(2-pyridyl)-3-pyridinecarbohydrazide,
22) 2-(1H-6-indazolylamino)-6-methyl-N-(3-pyridylcarbonyl)-3-pyridinecarbohydrazide, and
23) 2-(1H-6-indazolylamino)-6-methyl-3-(4-morpholinylcarbonyl)pyridine.

4. A process for preparing 6-methylnicotinamide derivatives according to claim 1 comprising the following steps of:

1) preparing 6-methylnicotinic acid derivatives (4) substituted with aminoindazole by heating and reacting 2-chloro-6-methylnicotinic acid (2) with 5-aminoindazole or 6-aminoindazole (3) in the presence of a base; and,
2) preparing 6-methylnicotinamide derivatives of formula 1 by activating the 6-methylnicotinic derivatives (4) prepared in step 1, and then reacting the compounds of formula 4 with amine compound (5);

Scheme 1

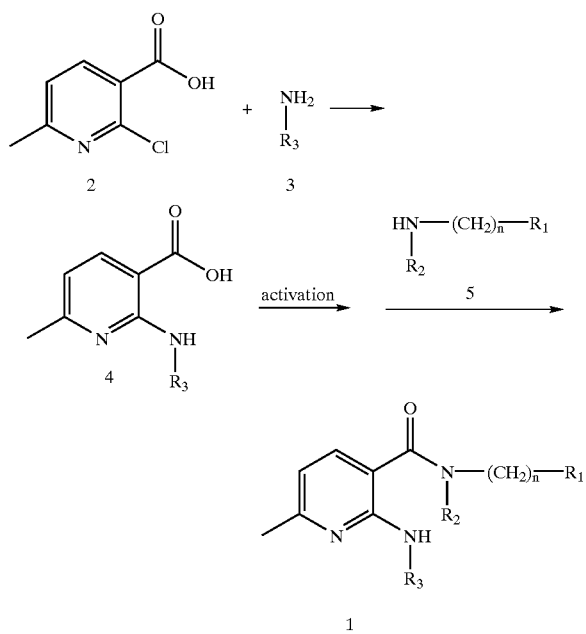

wherein, $R_1$, $R_2$, $R_3$ and n are defined in formula 1.

5. A therapeutic composition for hepatitis B, comprising 6-methylnicotinamide derivatives or their pharmaceutically acceptable salts of claim 1 as effective ingredients.

6. A therapeutic composition for hepatitis C, comprising 6-methylnicotinamide derivatives or their pharmaceutically acceptable salts of claim 1 as effective ingredients.

7. A therapeutic composition for acquired immune deficiency syndrome (AIDS), comprising 6-methylnicotinamide derivatives or their pharmaceutically acceptable salts of claim 1 as effective ingredients.

8. The process according to claim 4, wherein the activation is performed in form of highly reactive acid chloride compounds by adding excess thionyl chloride to the 6-methylnicotinic acid derivatives (4), subsequently heating or the activation is performed by Vilsmeier reagent prepared by heating thionyl chloride and N,N-dimethylformamide.

* * * * *